United States Patent
Bala et al.

(10) Patent No.: US 9,265,846 B2
(45) Date of Patent: Feb. 23, 2016

(54) AIR REMOVAL TEST STRIP

(71) Applicant: Dana Products, Inc., Franklin Park, IL (US)

(72) Inventors: Harry Bala, South Barrington, IL (US); Mark Bala, Chicago, IL (US)

(73) Assignee: American Sterilizer Company, Mentor, OH (US)

( * ) Notice: Subject to any disclaimer, the term of this patent is extended or adjusted under 35 U.S.C. 154(b) by 0 days.

(21) Appl. No.: 14/292,155

(22) Filed: May 30, 2014

(65) Prior Publication Data

US 2014/0273239 A1 Sep. 18, 2014

Related U.S. Application Data

(63) Continuation-in-part of application No. 13/687,888, filed on Nov. 28, 2012, now abandoned.

(51) Int. Cl.
*A61L 2/07* (2006.01)
*A61L 2/28* (2006.01)
*G01N 31/22* (2006.01)

(52) U.S. Cl.
CPC ... *A61L 2/07* (2013.01); *A61L 2/28* (2013.01); *G01N 31/226* (2013.01); *A61L 2202/24* (2013.01)

(58) Field of Classification Search
CPC .......... A61L 2/07; A61L 2/28; G01N 31/226
See application file for complete search history.

(56) References Cited

U.S. PATENT DOCUMENTS

| | | | | |
|---|---|---|---|---|
| 3,981,683 A | * | 9/1976 | Larsson et al. | 422/424 |
| 4,410,493 A | | 10/1983 | Joslyn | |
| 4,448,548 A | * | 5/1984 | Foley | 374/160 |
| 5,209,904 A | * | 5/1993 | Forney et al. | 422/73 |
| 5,378,430 A | * | 1/1995 | Nieves et al. | 422/426 |
| 5,895,627 A | | 4/1999 | Khachatoorian | |
| 7,718,125 B2 | * | 5/2010 | Bala | 422/550 |
| 7,740,802 B2 | | 6/2010 | Bala | |
| 7,790,105 B2 | * | 9/2010 | Bala | 422/401 |
| 7,811,516 B2 | | 10/2010 | Bala | |

FOREIGN PATENT DOCUMENTS

| | | |
|---|---|---|
| EP | 0022284 A1 | 1/1981 |
| WO | 9524622 A1 | 9/1995 |

OTHER PUBLICATIONS

The initial pages of the ANSI/AAMI/ISO 11140-4:2007 standards obtained from https://marketplace.aami.org/eseries/scriptcontent/docs/Preview%20Files/1114004_1208_preview.pdf.*
The initial pages of the ANSI/AAMI/ISO 11140-5:2007 standards obtained from https://marketplace.aami.org/eseries/scriptcontent/docs/Preview%20Files/1114005_1208_preview.pdf.*

(Continued)

*Primary Examiner* — Jill Warden
*Assistant Examiner* — Matthew Krcha
(74) *Attorney, Agent, or Firm* — Levenfeld Pearlstein, LLC

(57) ABSTRACT

An air removal test system for verifying adequate air removal during a sterilization cycle of a pre-vacuum type sterilizer includes specimen holder and a test strip. The test strip includes a solid indicator chemical, which liquefies and travels along a wicking element during the sterilization cycle. The test strip is configured to verify adequate removal of air during the sterilization cycle by displaying a color change through a window.

3 Claims, 2 Drawing Sheets

(56) References Cited

OTHER PUBLICATIONS

International Preliminary Report on Patenability for PCT/US2013/068464 dated Jun. 2, 2015.
International Search Report and Written Opinion for PCT/US14/68129 dated Jun. 24, 2015.
3M Sterilisation Steam Chemical Indicator Classifications, 2005 (retrieved on Mar. 26, 2015), Retrieved from the Internet and cited in ISR for PCT/US14/68129 dated Jun. 24, 2015 <URL:http://multimedia.3m.com/600678O/scic-tutorial-pdf.pdf>.

* cited by examiner

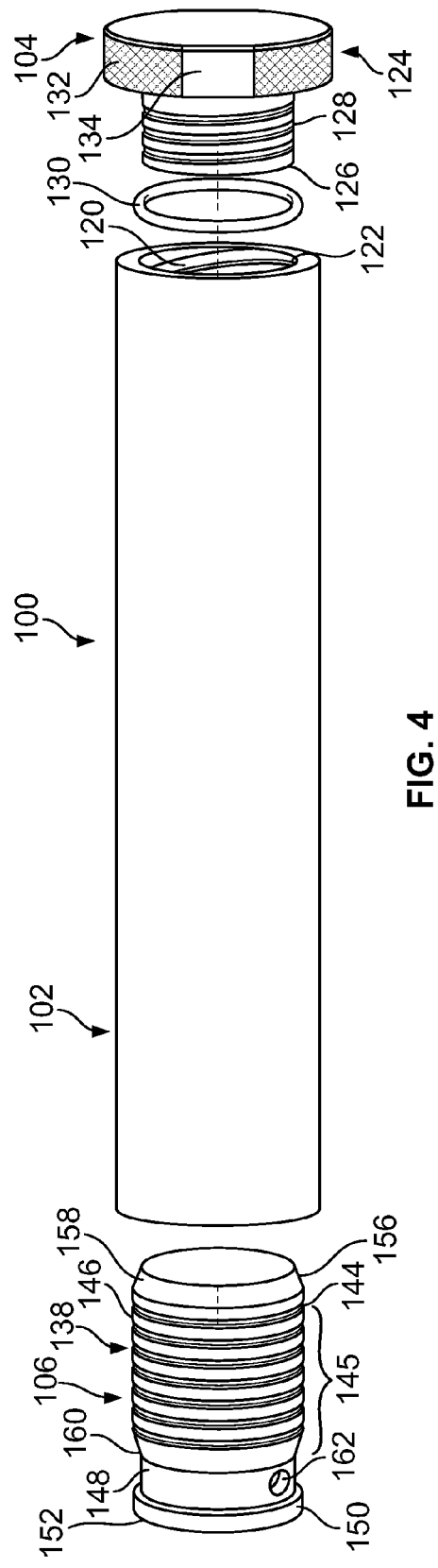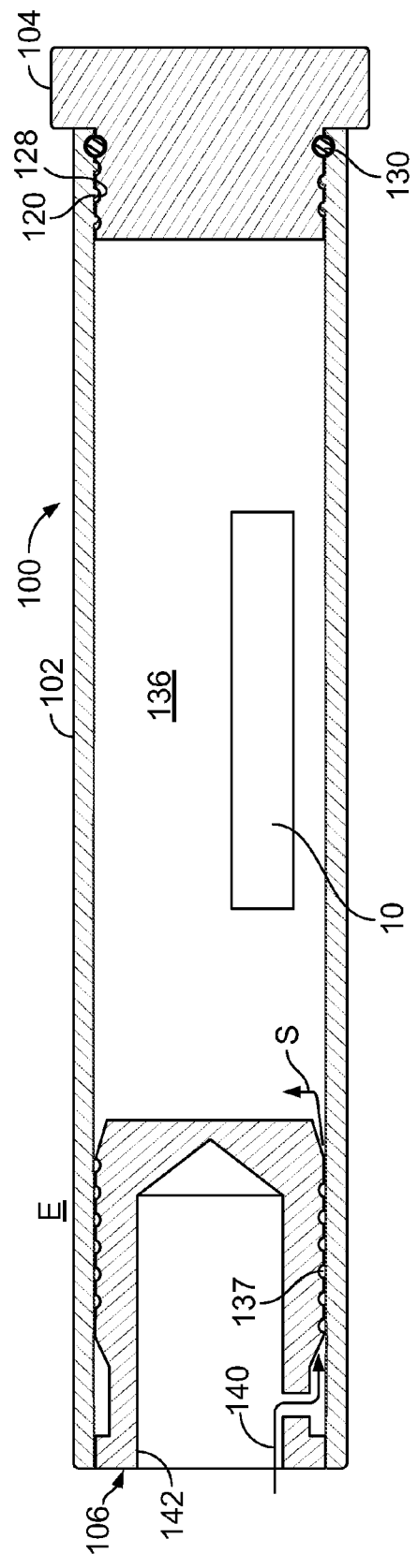

AIR REMOVAL TEST STRIP

CROSS-REFERENCE TO RELATED APPLICATION DATA

This application is a continuation-in-part of U.S. application Ser. No. 13/687,888, filed Nov. 28, 2012 entitled "Air Removal Test Strip", the contents of which are incorporated fully by reference herein.

BACKGROUND OF THE INVENTION

It is well known that heat destroys microorganisms. The presence of moisture accelerates this destruction by denaturing or coagulation of the proteins making up the microorganisms. Most microorganisms contain sufficient water so that moderate heat alone, e.g. 80° C.-100° C., will destroy the microorganism. Many bacterial spores, on the other hand, contain substantially no water and require elevated temperatures in excess of 150° C. for their destruction where dry heat is used. Hence, the destruction of such organisms is generally carried out in the presence of steam in steam sterilizers.

There are two basic types of steam sterilizers (autoclaves)—a gravity displacement autoclave and a prevacuum type sterilizer. In the gravity displacement autoclaves, steam is admitted at the top or the sides of the sterilizing chamber and, because the steam is lighter than air, forces air out the bottom of the chamber through a drain vent. Gravity displacement autoclaves are primarily used to process laboratory media, water, pharmaceutical products, regulated medical waste, and nonporous articles whose surfaces have direct steam contact. For gravity displacement sterilizers the penetration time into porous items is prolonged because of incomplete air elimination. For example, decontamination of 10 lbs of microbiological waste requires at least 45 minutes at 121° C., because the entrapped air remaining in a load of waste greatly retards steam permeation and heating efficiency.

Prevacuum type sterilizers are similar to the gravity displacement sterilizers except they are fitted with a vacuum pump (or ejector) to ensure air removal from the sterilizing chamber and load before the steam is admitted. By removing air, nearly instantaneous steam penetration can be provided even into porous loads.

Bowie-Dick type air removal tests are used to detect air leaks and inadequate air removal in prevacuum sterilizers. In the Bowie-Dick test, a commercially available Bowie-Dick-type test indicator is placed in the center of a test pack consisting of folded 100% cotton surgical towels prepared according to a standard test method, such as those found in American National Standards Institute (ANSI)/Association for the Advancement of Medical Instrumentation (AAMI)/International Organization for Standards (ISO) 11140. The test pack is placed horizontally in the front, bottom section of a sterilizer rack, near the door and over the drain, in an otherwise empty chamber, and the sterilizer is tested. Successful air removal is verified by a uniform color change in the Bowie-Dick-type test indicator after exposure to saturated steam at 132° C. or 134° C. for 3.5 min±5 sec and/or at 121° C. for 15 min±5 sec.

Inadequate air removal can result in an inadequate sterilization process, since air that is not removed from the chamber can interfere with steam contact. Thus, the air removal test is performed each day the vacuum-type steam sterilizer is used, before the first processed load. The test packs can be prepared using freshly laundered cotton surgical towels. ANSI/AAMI/ISO 11140 requires that the towels to be folded to a size 250 mm±30 mm in one direction and 300 mm±20 mm in the other direction, and that the height of the test pack to be between 250 mm and 280 mm. Thus, preparation for the air removal test for users can be labor intensive, time consuming and cost prohibitive. Disposable air removal test systems including disposable test packs have been developed, but they are still costly and create waste from disposing test packs after each use.

Therefore, there is a need for an improved air removal test system that can provide indication for successful air removal in prevacuum type sterilizers.

BRIEF SUMMARY OF THE INVENTION

Air removal test systems for verifying adequate air removal during a sterilization cycle of a pre-vacuum type sterilizer is provided according to various embodiments of the present disclosure. The air removal test systems are configured to simulate the test methods provided in ANSI/AAMI/ISO 11140-4:2007 and 11140-5:2007 without using the towel test packs specified in these test methods. The air removal test system of the present disclosure includes a specimen holder and a test strip, which is configured specific to the test method and sterilization cycle parameters to produce test results that are substantially equivalent to that produced using the test packs described in the test method.

The test strip according to various embodiments of the present disclosure is distinguishable from prior art steam sterilization indicators, such as those disclosed in Foley, U.S. Pat. No. 4,448,548, which is configured to indicate whether a predetermined temperature has been reached in a steam environment cycle. The Foley test strip is a Class 5 test strip. The test strip of the present disclosure is specifically configured to work with the specimen holder to simulate the tests described in ANSI/AAMI/ISO 11140-4:2007 and 11140-5:2007 to indicate whether air was adequately removed from a sterilizer during a sterilization cycle at predetermined parameters. The test strip of the present disclosure is a Class 2 test strip.

For example, ANSI/AAMI/ISO 11140-5:2007 requires that an indicator system when placed in the center of a specified test pack should show a non-uniform color change when the temperature at the center of the test pack is 2° C. lower than the temperature of the chamber drain at the beginning of the final 1 min of a 3.5 min cycle at 134° C., or at the beginning of the final 5 min of a 15 min cycle at 121° C. of the exposure phase of a sterilizer to indicate inadequate air removal. The air removal test system of the present disclosure is configured to simulate this test to produce test results that are substantially equivalent to the results obtained using the test pack and indicator system described in the test method to indicate whether air was adequately removed from a sterilizer during a sterilization cycle.

Further, the test strip of the present disclosure is configured specific to sterilization cycle parameters. That is, a test strip for a 134° C. or 132° C. for 3.5 min cycle may be configured differently than a test strip for 121° C. for 15 min cycle. Furthermore, prior art indicators, such as those disclosed in Foley, will not work to indicate adequate air removal even if they were placed in the specimen holder of the present disclosure.

In one aspect, an air removal test system for verifying adequate air removal during a sterilization cycle of a pre-vacuum type sterilizer is provided. The air removal test system includes a specimen holder and a test strip, which is configured to work in conjunction with the specimen holder to indicate whether an adequate air removal has occurred during a sterilization cycle in the pre-vacuum type sterilizer.

The specimen holder includes a tubular body defining an interior chamber, a closure cap sealable on a first end of the tubular body, and an end plug arranged in a second end of the tubular body. The end plug provides a single ingress and egress flow path into and out of the interior chamber.

The test strip includes a base element formed from a thermally conductive material having a length and a width and a recess formed therein, a solid indicator chemical deposited in the recess, a wicking element positioned at least in part in contact with the solid indicator chemical, a film layer positioned over the base element, the wicking element and the solid indicator chemical, and a coated paper disposed over the film layer. In this test strip configuration, the wicking element extends less than the length and width of the base element, and the coated paper includes a window therein. Further, the window is arranged away from the solid indicator chemical such that a portion of the wicking element is visible through the window. In use, the test strip is placed in the interior chamber, and the specimen holder with the test strip is place in the pre-vacuum type sterilizer, in which the solid indicator chemical liquefies and wicks along the wicking element during a pre-vacuum sterilization cycle and changes a color of the wicking element. The test strip is configured to verify an adequate air removal when the color change covers the portion of the wicking element visible through the window.

In one embodiment, the air removal test system is configured to simulate a test described in ANSI/AAMI/ISO 11140-4:2007 to indicate whether air was adequately removed during a sterilization cycle at 134° C. for 3.5 min±5 sec. In this embodiment, the test strip includes the film layer formed from a cast polypropylene having a thickness of about 2.2 mil, and the wicking element formed from a low-ash, qualitative paper having a basis weight of about 87.7 g/m$^2$ and a thickness of about 7.5 mil. Further, the test strip has a length of about 4.00 inches and a width of about 0.75 inches, and includes the window having a length of about 1.772 inches and a width of about 0.17 inches, which is arranged longitudinally away from a left end of the test strip at a distance of about 1.00 inches.

In another embodiment, the air removal test system is configured to simulate a test described in ANSI/AAMI/ISO 11140-4:2007 to indicate whether air was adequately removed during a sterilization cycle at 121° C. for 15 min±5 sec. In this embodiment, the test strip includes the film layer formed from a cast polypropylene having a thickness of about 1 mil, and the wicking element formed from a low-ash, qualitative paper having a basis weight of about 66 g/m2 and a thickness of about 7.3 mil. Further, the test strip has a length of about 4.00 inches and a width of about 0.75 inches, and includes the window having a length of about 1 inch and a width of about 0.17 inches, which is arranged longitudinally away from a left end of the test strip at a distance of about 0.875 inches.

In yet another embodiment, the air removal test system is configured to simulate a test described in ANSI/AAMI/ISO 11140-5:2007 to indicate whether air was adequately removed during a sterilization cycle at 132° C. or 134° C. for 3.5 min±5 sec. In this embodiment, the test strip includes the film layer formed from a cast polypropylene having a thickness of about 2.2 mil, and the wicking element formed from a low-ash, qualitative paper having a basis weight of about 87.7 g/m2 and a thickness of about 7.5 mil. Further, the test strip has a length of about 4.00 inches and a width of about 0.75 inches, and includes the window having a length of about 1.375 inches and a width of about 0.17 inches, which is arranged longitudinally away from a left end of the test strip at a distance of about 0.875 inches.

In another aspect, a method of verifying adequate air removal during a sterilization cycle of a pre-vacuum type sterilizer is provided. The method includes the step of introducing a test strip into a specimen holder, in which the test strip is configured to work in conjunction with the specimen holder to indicate whether an adequate air removal has occurred during a sterilization cycle in the pre-vacuum type sterilizer. The specimen holder includes a tubular body defining an interior chamber, a closure cap sealable on a first end of the tubular body, and an end plug arranged in a second end of the tubular body, in which the end plug provides a single ingress and egress flow path into and out of the interior chamber. The test strip includes a base element formed from a thermally conductive material having a length and a width and a recess formed therein, a solid indicator chemical deposited in the recess, a wicking element positioned at least in part in contact with the solid indicator chemical, a film layer positioned over the base element, the wicking element and the solid indicator chemical, and a coated paper disposed over the film layer. The wicking element of the test strip extends less than the length and width of the base element, and the coated paper includes a window therein. Further, the window is arranged away from the solid indicator chemical such that a portion of the wicking element is visible through the window.

The method also includes the steps of placing the specimen holder including the test strip in the pre-vacuum type sterilizer, running a sterilization cycle, and verifying an adequate air removal by inspecting a color change of the wicking element through the window.

In one embodiment, the method simulates a test described in ANSI/AAMI/ISO 11140-4:2007 to indicate whether air was adequately removed during a sterilization cycle at 134° C. for 3.5 min±5 sec. In this embodiment, the test strip includes the film layer formed from a cast polypropylene having a thickness of about 2.2 mil, and the wicking element formed from a low-ash, qualitative paper having a basis weight of about 87.7 g/m2 and a thickness of about 7.5 mil. Further, the test strip has a length of about 4.00 inches and a width of about 0.75 inches, and includes the window having a length of about 1.772 inches and a width of about 0.17 inches, which is arranged longitudinally away from a left end of the test strip at a distance of about 1.00 inches. An adequate air removal is verified when the color change covers the entire area of the wicking element visible through the window.

In another embodiment, the method simulates a test described in ANSI/AAMI/ISO 11140-4:2007 to indicate whether air was adequately removed during a sterilization cycle at 121° C. for 15 min±5 sec. In this embodiment, the test strip includes the film layer formed from a cast polypropylene having a thickness of about 1 mil, and the wicking element formed from a low-ash, qualitative paper having a basis weight of about 66 g/m2 and a thickness of about 7.3 mil. Further, the test strip has a length of about 4.00 inches and a width of about 0.75 inches, and includes the window having a length of about 1 inch and a width of about 0.17 inches, which is arranged longitudinally away from a left end of the test strip at a distance of about 0.875 inches. An adequate air removal is verified when the color change covers the entire area of the wicking element visible through the window.

In yet another embodiment, the method simulates a test described in ANSI/AAMI/ISO 11140-5:2007 to indicate whether air was adequately removed during a sterilization cycle at 132° C. or 134° C. for 3.5 min±5 sec. In this embodiment, the test strip includes the film layer formed from a cast polypropylene having a thickness of about 2.2 mil, and the wicking element formed from a low-ash, qualitative paper having a basis weight of about 87.7 g/m2 and a thickness of about 7.5 mil. Further, the test strip has a length of about 4.00 inches and a width of about 0.75 inches, and includes the window having a length of about 1.375 inches and a width of about 0.17 inches, which is arranged longitudinally away from a left end of the test strip at a distance of about 0.875 inches. An adequate air removal is verified when the color change covers the entire area of the wicking element visible through the window.

In another aspect, a test strip configured to work in conjunction with a specimen holder to verify adequate air removal during a sterilization cycle of a pre-vacuum type sterilizer is provided. The test strip includes a base element formed from a thermally conductive material having a length and a width and a recess formed therein, a solid indicator chemical deposited in the recess, a wicking element positioned at least in part in contact with the solid indicator chemical, a film layer positioned over the base element, the wicking element and the solid indicator chemical, and a coated paper disposed over the film layer. The wicking element of the test strip extends less than the length and width of the base element, and the coated paper includes a window therein. Further, the window is arranged away from the solid indicator chemical such that a portion of the wicking element is visible through the window. The test strip is configured to verify an adequate air removal during a predetermined sterilization cycle when the test strip is placed in an inner chamber of the specimen holder and placed in the pre-vacuum type sterilizer during the sterilization cycle, in which the adequate air removal is verified when a color change from liquefied indicator chemical wicking along the wicking element covers the entire area of the wicking element visible through the window.

In one embodiment, the test strip is configured for a test described in ANSI/AAMI/ISO 11140-4:2007 to indicate whether air was adequately removed during a sterilization cycle at 134° C. for 3.5 min±5 sec. In this embodiment, the test strip includes the film layer formed from a cast polypropylene having a thickness of about 2.2 mil, and the wicking element formed from a low-ash, qualitative paper having a basis weight of about 87.7 g/m2 and a thickness of about 7.5 mil. Further, the test strip has a length of about 4.00 inches and a width of about 0.75 inches, and includes the window having a length of about 1.772 inches and a width of about 0.17 inches, which is arranged longitudinally away from a left end of the test strip at a distance of about 1.00 inches.

In another embodiment, the test strip is configured for a test described in ANSI/AAMI/ISO 11140-4:2007 to indicate whether air was adequately removed during a sterilization cycle at 121° C. for 15 min±5 sec. In this embodiment, the test strip includes the film layer formed from a cast polypropylene having a thickness of about 1 mil, and the wicking element formed from a low-ash, qualitative paper having a basis weight of about 66 g/m2 and a thickness of about 7.3 mil. Further, the test strip has a length of about 4.00 inches and a width of about 0.75 inches, and includes the window having a length of about 1 inch and a width of about 0.17 inches, which is arranged longitudinally away from a left end of the test strip at a distance of about 0.875 inches.

In yet another embodiment, the test strip is configured for a test described in ANSI/AAMI/ISO 11140-5:2007 to indicate whether air was adequately removed during a sterilization cycle at 132° C. or 134° C. for 3.5 min±5 sec. In this embodiment, the test strip includes the film layer formed from a cast polypropylene having a thickness of about 2.2 mil, and the wicking element formed from a low-ash, qualitative paper having a basis weight of about 87.7 g/m2 and a thickness of about 7.5 mil. Further, the test strip has a length of about 4.00 inches and a width of about 0.75 inches, and includes the window has a length of about 1.375 inches and a width of about 0.17 inches, which is arranged longitudinally away from a left end of the test strip at a distance of about 0.875 inches.

In any of the foregoing embodiments, the base element of the test strip may be formed from aluminum having a thickness of about 3 mils, and may include an acrylic adhesive backing. Further, the coated paper may include an acrylic coating thereon. In some embodiments, the test strip may be configured to verify an adequate air removal when the color change covers the entire area of the wicking element visible through the window.

These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings, wherein:

FIG. 4 is an exploded view of a specimen holder according to an embodiment; and

FIG. 5 is a cross-sectional view of the specimen holder of FIG. 4.

DETAILED DESCRIPTION OF THE INVENTION

Figure 1:
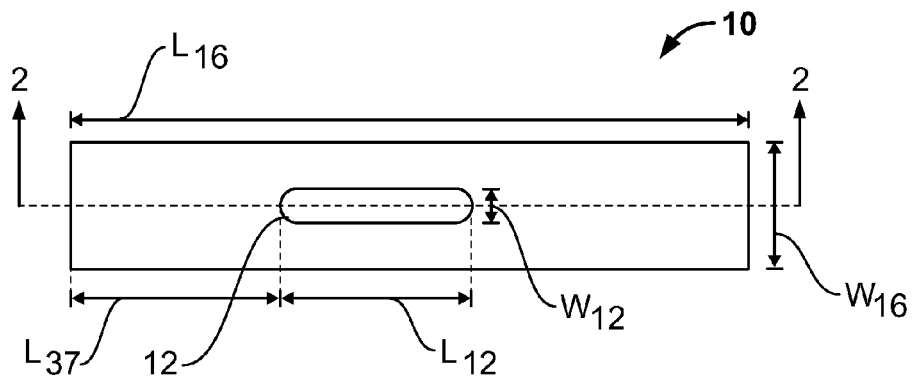
FIG. 1 is a top plan view of an air removal test strip according to an embodiment.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

Figure 2:
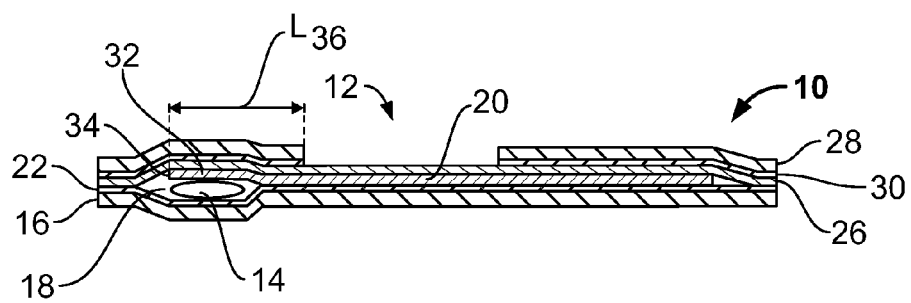
FIG. 2 is a cross-sectional view taken along line 2-2 of FIG. 1.
Figure 3:
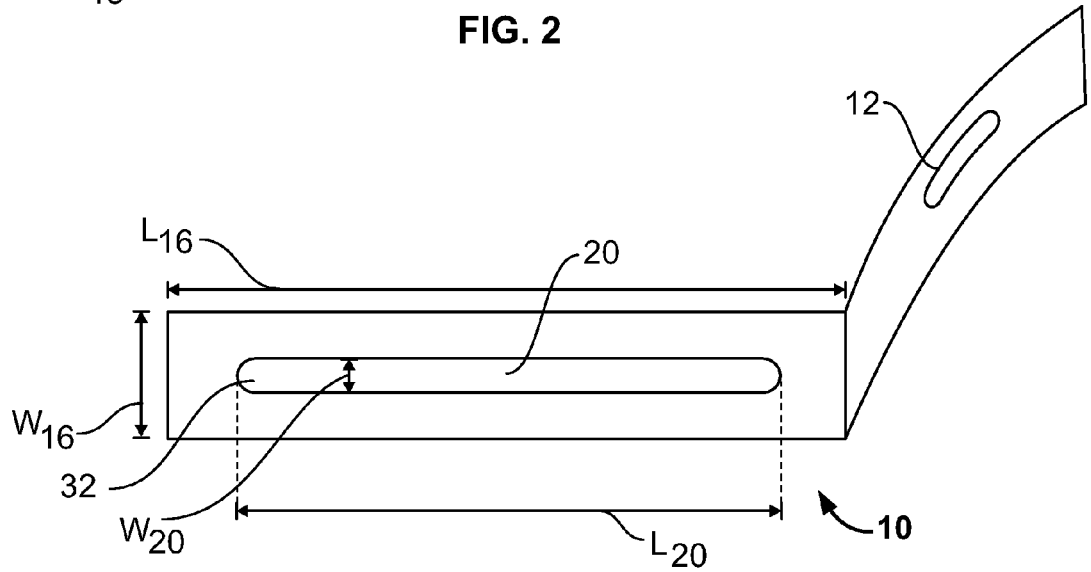
FIG. 3 is a top perspective view of the test strip of FIG. 1 with a paper layer, an adhesive layer, and a film layer peeled off.

FIGS. 1-3 show an embodiment of a test strip 10 for detecting air leaks and inadequate air removal in a pre-vacuum type sterilizer. The test strip 10 is configured to work in conjunction with a reusable specimen holder, such as those disclosed in U.S. Pat. Nos. 7,718,125, 7,740,802, 7,790,105, and 7,811,516, which are commonly assigned to the assignee of the present application, the entire contents of which are incorporated herein by reference, to simulate the air removal tests described in ANSI/AAMI/ISO 11140-4:2007 and 11140-5:2007. A specimen holder 100 according to an embodiment is shown in FIGS. 4-5. In use, the test strip 10 is placed in the specimen holder 100 as shown in FIG. 5, which is then placed in a pre-vacuum type sterilizer for a pre-vacuum sterilization cycle to determine whether an adequate air removal in the sterilization has been achieved.

As shown in FIG. 1, the test strip 10 has an open window 12 through which the wicking of an indicator chemical 14 (FIG. 2) can be observed to determine whether adequate air removal in the prevacuum has occurred as will be described below. FIG. 2 is a cross-sectional illustration of the strip 10. The test strip 10 generally includes a base element 16, an adhesive layer 22, a wicking element 20, a film layer 26, an adhesive layer 30, a paper layer 28, and a solid indicator chemical 14. The base element 16 is formed from a foil or other high-heat transfer material. The adhesive layer 22 is provided on the base element 16 as a continuous layer covering substantially the entire top surface of the base element 16. The base element 16 has a length $L_{16}$ and a width $W_{16}$. In this embodiment, the base element 16 is formed from an aluminum foil. A depression or recess 18 is formed in the base element 16 and the adhesive layer 22. The indicator chemical 14, which is a temperature sensitive chemical formulation, is provided in the recess 18 between the adhesive layer 22 and the wicking element 20.

The wicking element 20, such as a wicking paper is positioned on the base element 20 attached by the adhesive layer 22. FIG. 3 shows a top view of the strip with the film layer 26, the adhesive layer 30, and the paper layer 28 peeled away to illustrate the wicking element 20 arranged on the base element 20 and the adhesive layer 22. As shown, the wicking element 20 has a width $W_{20}$ and a length $L_{20}$ that is less than the width $W_{16}$ and the length $L_{16}$ of the base element 16. The wicking element 20 is generally centered on the base element 16 and over the indicating chemical 14 in the recess 18, such that an end portion 32 of the wicking element 20 is in contact with the indicator chemical 14. The wicking element 20 extends longitudinally along the base element 16, such that at least some portion of the wicking element is securely attached to the base element 20 by the adhesive layer 22. In this manner, the indicator chemical 14 and the wicking element 20 are bounded within the four sides of the test strip 10.

The film 26 is applied over the wicking element 20, and adhered to the base element 16 by the adhesive layer 22. The film 26 has substantially the same width and length as the base element 16, and thus, it is attached to the base element 16 by the adhesive layer 22 in the peripheral areas around the wicking element 20. The film 26 is a transparent film, as will be discussed in more detail below. The paper layer 28 is provided with the adhesive layer 30, and applied over the film 26. The paper layer 28 and the adhesive layer 30 include the window 12 that is cut out (as seen in FIGS. 1-3) to allow for visual indication within the window 12, through the film 26.

In exemplary test strips 10, the foil element 16 and the adhesive layer 22 are formed using a 3/1000 inch (3 mil) thick adhesive label. The adhesive layer 22 on the foil 16 (to adhere to the wicking element 20 and the film 26) is an acrylic adhesive. The paper layer 28 and the adhesive layer 30 are formed from an acrylic coated paper.

The film layer 26 is formed from a cast polypropylene having a thickness of about 1 mil or about 2.0 to 2.2 mils or 3.0 to 3.2 mils. The wicking element 20 is formed from a suitable wicking material, for example, a wicking material commercially available from Whatman Inc. of Piscataway, N.J. under the product identifier Whatman 1. In some embodiments, the wicking element 20 may be formed from a low-ash, qualitative paper having a basis weight of about 66 grams per square meter (g/m$^2$) and a caliper or thickness of about 7.3 thousandths of an inch (mil), or a low-ash, qualitative paper having a basis weight of about 87.7 grams per square meter (g/m$^2$) and a caliper or thickness of about 7.5 thousandths of an inch (mil), or from a white, smooth surface, cotton paper having a basis weight of about 186 g/m$^2$ and a caliper or thickness of about 13.3 mils.

The indicator chemical 14 is salicylamide, ethoxy benzomide or a similar chemical, having a colorant added in a concentration of about 0.01 percent by weight. An example of one colorant is a blue color dye.

The window 12, which is formed in the paper layer 28 and the adhesive layer 30, extends over an area of the surface of the paper layer 28 less than the entirety of the length of the paper 28. Further, the window 12 has a length $L_{12}$ and a width $W_{12}$, which are less than the length $L_{20}$ and the width $W_{20}$ of the wicking element 20. The window 12 is arranged over the wicking element 20, such that only a portion of the wicking element 20 is visible through the film layer 26 and the window 12.

The test strip 10 is configured such that when the test strip 10 is inserted in the specimen holder 100 and placed in a pre-vacuum type sterilizer chamber, the test strip 10 can indicate whether adequate air removal has occurred during a sterilization cycle, which provides saturated steam at 132° C. or 134° C. for 3.5 min±5 sec and/or at 121° C. for 15 min±5 sec, as does a Bowie-Dick-type test indicator system prepared according to ANSI/AAMI/ISO 11140-4:2007 or 11140-5:2007. During a sterilization cycle, the indicator chemical 14 liquefies and wicks along the wicking material 20. In preferred embodiments, adequate air removal is verified when the liquefied indicator chemical wicks passed the window 12. That is, the color of the liquefied indicator chemical, for example, blue, cover substantially the entire portion of the wicking material 20 visible through the window 12 to indicate that air has been adequately removed from the sterilizer chamber during a pre-vacuum sterilizing cycle. Therefore, the window 12 is sized and arranged at a precalculated distance from the location of the indicator chemical 14 according to particular pre-vacuum steam sterilization parameters.

The test strip 10 is configured specific to sterilization cycle parameters. For example, the test strip 10 may be configured to have a length $L_{16}$ of about 4 inches and a width $W_{i6}$ of about ¾ inches. The wicking element 20 may have a length $L_{20}$ of about 3 ⅜ inches and a width $W_{16}$ of about ¼ inches, and arranged generally in the middle of the base element 16 as shown in FIG. 3. The indicator chemical 14 may be placed under the end portion 32 of the wicking element 20 as shown in FIG. 2. The window 12 may have a length $L_{12}$ of about 1 inch to about 1.8 inches and a width $W_{12}$ of about 3/16 inches, and arranged longitudinally away from the indicator chemical 14. In one embodiment, the window 12 is positioned away from an end 34 of the wicking element 20 a distance $L_{36}$ of about 15/16 inches. The window 12 is arranged over the wicking element 20, such that the wicking of the liquefied indicator chemical 14 can be observed through the window 12. Adequate air removal during a steam sterilization cycle may be verified when the color change or a dark bar formed from the wicking of the liquefied indicator chemical covers substantially the entire area of the wicking element 20 visible through the window 12.

Various embodiments of the test strip 10 can be configured to work with reusable specimen holders, such as sterilization challenge specimen holders disclosed in U.S. Pat. Nos. 7,718,125, 7,740,802, 7,790,105, and 7,811,516, the entire contents of which are incorporated herein by reference. An exemplary specimen holder 100 is shown in FIGS. 4-5. The holder 100 includes a hollow tubular body 102, a closure cap 104 and an end plug 106. The body 102 can be covered or enveloped in an insulating layer (not shown.)

The body 102 includes an internal thread 120 at one open end 122. The closure cap 104 includes a gripping portion 124 and a depending plug 126 having an external thread 128 (to mate to the threaded 120 opening) to close the holder 100. A seal 130 such as the illustrated O-ring can fitted onto the cap 104 to provide a gas-tight seal between the closure cap 104 and the body 102. In a present holder 100, the gripping portion 124 is textured or knurled (as indicated at 132) to facilitate rotating or turning the cap 104. The gripping portion 124 can include a flattened portion (a flat 134) so that when the holder 100 is laid on its side, it will be prevented from rolling.

The end plug 106 provides a single ingress and egress flow path into and out of the interior or chamber 136 when the cap 104 is in place on the body 102 and permits drawing a vacuum in the holder 100 and introducing a sterilization fluid, such as steam, into to the holder 100 in a controlled manner. The plug 106 includes a body 138 having a recess or well 140 formed therein that defines an inner wall 142. The body 138 includes a spiral formed channel or groove 144 in an outer wall 146 thereof. The outer wall 146 includes a peripheral recess or channel 148 formed adjacent to a sealing lip 150 at an end 152 of the plug 106.

The spiral formed channel 144 opens at a first end 152 into the peripheral recess 148 and spirals around the body 138 extending to about the opposite end 156 of the plug 106. In a present plug 106, the opposite end 156 (which is the end at the chamber 136 side of the plug 106), includes a chamfer 158 at which the spiral formed groove 144 ends. In a present plug 106, the transition from the peripheral channel 148 to the grooved region 145 is also chamfered as indicated at 160.

The plug 106 includes an opening 162 through the wall 146 at the peripheral recess 148. The opening 162 provides communication between outside of the holder 100 (the environs E) and the interior or chamber 136 of the holder 100. Communication is provided from the environs E, through the opening 162, into the recess 148, through the spiral groove 144 and into the chamber 136. The chamfers 158, 160 at both ends of the spiral groove 144 (or grooved region 145) provide for a smooth transition into and out of the groove 144 and prevent excessive resistance to flow through the groove 144. The groove 144, is smooth, as by being formed by machining, but provides a tortuous ingress and egress path between the environs E and the chamber 136.

The plug 106 is friction fitted into the chamber body 102. In this manner the lip 150 is snug up to the interior wall 137 of the body 102 and provides an external seal between the environs E and the peripheral recess 148. Moreover the plug body outer wall 146, at the grooved region 145 (between the chamfers 158, 160) also is snug up to the interior wall 137 of the body 102 and provides a seal between the recess 148 and the chamber 136 and the groove 144. It will be appreciated that the interior wall 137 of the body, at the plug 106 is smooth, unlike the threads 120 formed in the cap 104 end. In that there is no machining necessary at interior wall 137 the smooth surface (unlike threads) proper "mating" of the plug 106 and body 102 is enhanced.

A present holder 100 is formed from aluminum. Many different materials are contemplated for use, including various other metals, steels, alloys and the like. Suitable polymers may also be used, as will be appreciated by those skilled in the art. Due to the thermal conditions to which the holder 100 is subjected, each of the parts of the present holder 100 (the body 102, the cap 104 and the plug 106) is preferably formed from a similar material. This is to prevent the parts from expanding and contracting at different rates, and in different proportions from one another. It is also contemplated that different materials having similar thermal properties can also be used, where appropriate.

It will also be appreciated from the above-provided discussion that the spiral groove 144 is formed or machined to within a fairly tight tolerance. In a present holder 100, a plug 106 having an overall length of about 1 inch is formed with a groove 144 having a cross-sectional area of 0.00031 inches$^2$. The groove 144 is formed using a $\frac{1}{16}$ inch grooving tool having a rounded or curved profile, and cut to a depth of about 0.011 inches±0.0005 inches (about $\frac{1}{3}$ of a circle having a $\frac{1}{16}$ inch diameter). The groove 144 has width of about 0.045 inches. Cross-sectional areas of up to about 0.001 inches$^2$ can be used, however, the length of the plug 106 (and the spiral groove 144) is formed commensurately longer. For example, in a groove 144 having a cross-sectional area of 0.000553 inches$^2$, the groove 144 is formed in a plug 106 having a length of about 2 inches (compared to a 1 inch plug 106 for the 0.00031 inches$^2$ area). It has been found that the cross-sectional area of the groove 144 is best formed at less than about 5.5 E-4 inches$^2$. The grooves 144 are formed in the plug 106 at a rate (density) of about 10 turns per linear inch of plug 106.

In use, the test strip 10 is placed in the holder 100 and the holder 100 is placed inside of the sterilizer chamber. The sterilizer chamber is evacuated and steam is then introduced into the device. Following a sterilization cycle, the specimen holder 100 is removed from the sterilizer chamber, and the test strip 10 is checked to verify whether air was adequately evacuated during the sterilization cycle as described before.

In one embodiment, a test strip is configured to work in conjunction with the specimen holder 100 to simulate the test described in ANSI/AAMI/ISO 11140-4:2007. In this embodiment the test strip 10 is configured to produce the substantially same test results as the test performed according to ANSI/AAMI/ISO 11140-4:2007 using the specified test pack to indicate whether air was adequately removed during a sterilization cycle at 134° C. for 3.5 min±5 sec. The test strip for the sterilization cycle at 134° C. for 3.5 min±5 sec is similarly configured as the test strip 10 of FIGS. 1-3. The test strip includes a base element 16 and an adhesive layer 22, which are formed from an aluminum foil adhesive label having a thickness of about 3 mil. The adhesive layer 22 is an acrylic adhesive. An indicator chemical 14 is salicylamide. The test strip also includes a film layer 26 formed from a cast polypropylene having a thickness of about 2.2 mil, and a wicking element 20 formed from a low-ash, qualitative paper having a basis weight of about 87.7 g/m2 and a thickness of about 7.5 mil. Further, the test strip includes a paper layer 28 and an adhesive layer 30, which are formed from an acrylic coated paper. The test strip has a length L16 of about 4.00 inches and a width W16 of about 0.75 inches. The window 12 has a length L12 of about 1.772 inches and a width W12 of about 0.17 inches, and is arranged longitudinally away from the indicator chemical 14. In this embodiment, the window 12 is positioned away from the left end of the test strip at a distance L37 of about 1.00 inches. Adequate air removal during a steam sterilization cycle at 134° C. for 3.5 min±5 sec is verified when the color change or a dark bar formed from the wicking of the liquefied indicator chemical covers substantially the entire area of the wicking element 20 visible through the window 12.

In another embodiment, a test strip is configured to work in conjunction with the specimen holder 100 to simulate the test described in ANSI/AAMI/ISO 11140-5:2007. In this embodiment the test strip 10 is configured to produce the substantially same test results as the test performed according to ANSI/AAMI/ISO 11140-5:2007 using the specified test pack to indicate whether air was adequately removed during a sterilization cycle at 132° C. or 134° C. for 3.5 min±5 sec. The test strip for the sterilization cycle at 132° C. or 134° C. for 3.5 min±5 sec for ANSI/AAMI/ISO 111140-5:2007 is similarly configured as the above described test strip for the sterilization cycle at 134° C. for 3.5 min±5 sec for ANSI/AAMI/ISO 11140-4:2007, except the size and placement of the window 12. In this embodiment, the window 12 has a length L12 of about 1.375 inches and a width W12 of about 0.17 inches, and is arranged away from the left end of the test strip at a distance L37 of about 0.875 inches.

In yet another embodiment, a test strip is configured to work in conjunction with the specimen holder 100 to simulate the test described in ANSI/AAMI/ISO 11140-4:2007. In this embodiment the test strip 10 is configured to produce the substantially same test results as the test performed according to ANSI/AAMI/ISO 11140-4:2007 using the specified test pack to indicate whether air was adequately removed during a sterilization cycle at 121° C. for 15 min±5 sec. The test strip for the sterilization cycle at 121° C. for 15 min±5 sec for ANSI/AAMI/ISO 11140-4:2007 is similarly configured as the above described test strip for the sterilization cycle at 134° C. for 3.5 min±5 sec for ANSI/AAMI/ISO 11140-4:2007, except the film layer 26, the wicking element 20 and the size and placement of the window 12. In this embodiment, the film layer 26 is formed from a cast polypropylene having a thickness of about 1 mil, and a wicking element 20 is formed from a low-ash, qualitative paper having a basis weight of about 66 g/m2 and a thickness of about 7.3 mil. The window 12 has a length L12 of about 1.00 inches and a width W12 of about 0.17 inches, and is arranged away from the left end of the test strip at a distance L37 of about 0.875 inches.

All patents referred to herein, are hereby incorporated herein by reference, whether or not specifically done so within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover all such modifications as fall within the scope of the invention.

What is claimed is:

1. A method of verifying adequate air removal during a sterilization cycle of a pre-vacuum type sterilizer, comprising:
   introducing a Class 2 test strip into a specimen holder including a tubular body defining an interior chamber, a closure cap sealable on a first end of the tubular body, and an end plug arranged in a second end of the tubular body, wherein the end plug provides a single ingress and egress flow path into and out of the interior chamber; wherein the test strip is configured to work in conjunction with the specimen holder to indicate whether an adequate air removal has occurred during a sterilization cycle in the pre-vacuum type sterilizer, the test strip having:
      a base element formed from a thermally conductive material having a length and a width, the base element having a recess formed therein;
      a solid indicator chemical deposited in the recess;
      a wicking element positioned at least in part in contact with the solid indicator chemical, the wicking element extending less than the length and width of the base element;
      a film layer positioned over the base element, the wicking element and the solid indicator chemical; and
      a coated paper disposed over the film layer, the coated paper including a window therein,
      wherein the window is arranged away from the solid indicator chemical such that a portion of the wicking element is visible through the window;
   placing the specimen holder including the test strip in the pre-vacuum type sterilizer;
   running a pre-vacuum sterilization cycle; and
   verifying an adequate air removal by inspecting a color change of the wicking element through the window, the color change of the wicking element being in response to adequate removal of air from the specimen holder after exposure to saturated stead
   wherein the method simulates a test described in ANSI/AAMI/ISO 11140-4:2007 to indicate whether air was adequately removed during a sterilization cycle at 134° C. for 3.5 min ±5 sec, wherein the test strip includes the film layer formed from a cast polypropylene having a thickness of about 2.2 mil, and the wicking element formed from a low-ash, qualitative paper having a basis weight of about 87.7 g/m² and a thickness of about 7.5 mil, wherein the test strip has a length of about 4.00 inches and a width of about 0.75 inches, wherein the window has a length of about 1.772 inches and a width of about 0.17 inches, and is arranged longitudinally away from a left end of the test strip at a distance of about 1.00 inches, wherein an adequate air removal is verified when the color change covers the entire area of the wicking element visible through the window.

2. A method of verifying adequate air removal during a sterilization cycle of a pre-vacuum type sterilizer, comprising:
   introducing a Class 2 test strip into a specimen holder including a tubular body defining an interior chamber, a closure cap sealable on a first end of the tubular body, and an end plug arranged in a second end of the tubular body, wherein the end plug provides a single ingress and egress flow path into and out of the interior chamber; wherein the test strip is configured to work in conjunction with the specimen holder to indicate whether an adequate air removal has occurred during a sterilization cycle in the pre-vacuum type sterilizer, the test strip having:
      a base element formed from a thermally conductive material having a length and a width, the base element having a recess formed therein;
      a solid indicator chemical deposited in the recess;
      a wicking element positioned at least in part in contact with the solid indicator chemical, the wicking element extending less than the length and width of the base element;
      a film layer positioned over the base element, the wicking element and the solid indicator chemical; and
      a coated paper disposed over the film layer, the coated paper including a window therein,
      wherein the window is arranged away from the solid indicator chemical such that a portion of the wicking element is visible through the window;
   placing the specimen holder including the test strip in the pre-vacuum type sterilizer;
   running a pre-vacuum sterilization cycle; and
   verifying an adequate air removal by inspecting a color change of the wicking element through the window, the color change of the wicking element being in response to adequate removal of air from the specimen holder after exposure to saturated stead
   wherein the method simulates a test described in ANSI/AAMI/ISO 11140-4:2007 to indicate whether air was adequately removed during a sterilization cycle at 121° C. for 15 min ±5 sec, wherein the test strip includes the film layer formed from a cast polypropylene having a thickness of about 1 mil, and the wicking element formed from a low-ash, qualitative paper having a basis weight of about 66 g/m$^2$ and a thickness of about 7.3 mil, wherein the test strip has a length of about 4.00 inches and a width of about 0.75 inches, wherein the window has a length of about 1 inch and a width of about 0.17 inches, and is arranged longitudinally away from a left end of the test strip at a distance of about 0.875 inches, wherein an adequate air removal is verified when the color change covers the entire area of the wicking element visible through the window.

3. A method of verifying adequate air removal during a sterilization cycle of a pre-vacuum type sterilizer, comprising:
introducing a Class 2 test strip into a specimen holder including a tubular body defining an interior chamber, a closure cap sealable on a first end of the tubular body, and an end plug arranged in a second end of the tubular body, wherein the end plug provides a single ingress and egress flow path into and out of the interior chamber; wherein the test strip is configured to work in conjunction with the specimen holder to indicate whether an adequate air removal has occurred during a sterilization cycle in the pre-vacuum type sterilizer, the test strip having:
   a base element formed from a thermally conductive material having a length and a width, the base element having a recess formed therein;
   a solid indicator chemical deposited in the recess;
   a wicking element positioned at least in part in contact with the solid indicator chemical, the wicking element extending less than the length and width of the base element;
   a film layer positioned over the base element, the wicking element and the solid indicator chemical; and
   a coated paper disposed over the film layer, the coated paper including a window therein,
   wherein the window is arranged away from the solid indicator chemical such that a portion of the wicking element is visible through the window;
placing the specimen holder including the test strip in the pre-vacuum type sterilizer;
running a pre-vacuum sterilization cycle; and
verifying an adequate air removal by inspecting a color change of the wicking element through the window, the color change of the wicking element being in response to adequate removal of air from the specimen holder after exposure to saturated stead
wherein the method simulates a test described in ANSI/AAMI/ISO 11140-5:2007 to indicate whether air was adequately removed during a sterilization cycle at 132° C. or 134° C. for 3.5 min ±5 sec, wherein the test strip includes the film layer formed from a cast polypropylene having a thickness of about 2.2 mil, and the wicking element formed from a low-ash, qualitative paper having a basis weight of about 87.7 g/m$^2$ and a thickness of about 7.5 mil, wherein the test strip has a length of about 4.00 inches and a width of about 0.75 inches, wherein the window has a length of about 1.375 inches and a width of about 0.17 inches, and is arranged longitudinally away from a left end of the test strip at a distance of about 0.875 inches, wherein an adequate air removal is verified when the color change covers the entire area of the wicking element visible through the window.

* * * * *

UNITED STATES PATENT AND TRADEMARK OFFICE
CERTIFICATE OF CORRECTION

PATENT NO. : 9,265,846 B2  
APPLICATION NO. : 14/292155  
DATED : February 23, 2016  
INVENTOR(S) : Harry Bala et al.

Page 1 of 1

It is certified that error appears in the above-identified patent and that said Letters Patent is hereby corrected as shown below:

Title page

Item (56) Other Publications, Page 2, Column 1, line 1, "Patenability" to read as --Patent ability--.

Specification

Column 3, line 27, "AAAMI" to read as --AAMI--.

Column 8, line 31, "Wi6" to read as --W16--.

Column 9, line 28, "groove144" to read as --groove 144--.

Signed and Sealed this  
Nineteenth Day of July, 2016

Michelle K. Lee  
*Director of the United States Patent and Trademark Office*